United States Patent [19]

Schindler et al.

[11] Patent Number: 4,473,644

[45] Date of Patent: Sep. 25, 1984

[54] ACID STABLE PROTEASE FROM MUTANTS OF GENUS RHIZOPUS

[75] Inventors: Joachim Schindler, Hilden; Friedhelm Bartnik; Rolf Schmid, both of Duesseldorf; Albrecht Weiss, Erkrath, all of Fed. Rep. of Germany

[73] Assignee: Henkel Kommanditgesesllschaft auf Aktien, Dusseldorf, Fed. Rep. of Germany

[21] Appl. No.: 409,122

[22] Filed: Aug. 18, 1982

[30] Foreign Application Priority Data

Aug. 20, 1981 [DE] Fed. Rep. of Germany ....... 3132936

[51] Int. Cl.³ .................... C12N 15/00; C12N 9/58; C12N 1/14; C12R 1/845
[52] U.S. Cl. ................... 435/172.1; 435/223; 435/254; 435/939
[58] Field of Search .............. 435/172, 219–225, 435/254; 426/63

[56] References Cited

U.S. PATENT DOCUMENTS 3,031,380 4/1962 Minagawa et al. ............. 435/222 X
4,062,732 12/1977 Lehmann et al. ............... 435/223 X

OTHER PUBLICATIONS

Rose, editor Economic Microbiology, vol. 5, Microbial Enzymes and Bioconversions, 1980, pp. 142–143.

*Primary Examiner*—Lionel M. Shapiro
*Attorney, Agent, or Firm*—Ernest G. Szoke; Henry E. Millson, Jr.; Mark A. Greenfield

[57] ABSTRACT

Process for the preparation of acid stable protease having a broad activity spectrum by culturing selected mutants of *Rhizopus rhizopodiformis* CBS 227.75 under aerobic conditions in a nutrient medium containing assimilable carbon and nitrogen sources, at a pH between 3 and 7 and at a temperature between 25° C. and 50° C., and separating the resulting protease enzyme; the mutants used in the process together with a process for preparation of the mutants.

7 Claims, No Drawings

ACID STABLE PROTEASE FROM MUTANTS OF GENUS RHIZOPUS

BACKGROUND OF THE INVENTION

U.S. Pat. No. 4,062,732 issued Dec. 13, 1977 to Lehmann et al discloses a process for producing an acid stable protease with a broad activity spectrum by culturing a fungus strain of the species *Rhizopus rhizopodiformis* isolated from earth samples. The fungus strain has the depository number CBS 227.75 and is deposited in the Centraal Bureau voor Schimmel-Cultures in Baarn (the Netherlands).

DETAILED DESCRIPTION OF THE INVENTION

The present invention has for its object the enhancement of protease yield from strains of the genus Rhizopus, which is achieved in accordance with the invention by mutation of fungus strains thereof and selection of suitable mutants from those obtained by the mutation procedure.

The process of the invention results in the production of high yields of acid stable protease having a broad pH-activity range. This process is carried out by culturing under aerobic conditions a mutant of a fungus strain of the genus Rhizopus having a proteolytic activity of >10 mTU/ml, preferably at least 21 mTU/ml, in agitated cultures in a nutrient medium containing assimilable carbon and nitrogen sources at a pH between about 3 and about 7 and at a temperature between about 25° C. and about 50° C., and separating the resulting protease enzyme.

The mutant strains having the required proteolytic activity which are used in the above process are preferably obtained by UV-irradiation. The mutation process can be repeated one or more times by selecting and culturing mutants that exhibit enhanced protease forming ability.

The present invention also relates to those mutants of the parent strains that show a proteolytic activity of >10 mTU/ml, preferably at least 21 mTU/ml, in agitated cultures and which produce protease with characteristics identical to those of protease obtained from the wild strain Rhizopus CBS 227.75 on the basis of the tests described below (isoelectrofocussing and immunological testing). This aspect of the invention relates in particular to the following mutants:

*Rhizopus rhizopodiformis* III-34 (CBS 219.80)
*Rhizopus rhizopodiformis* III-46 (CBS 220.80)
*Rhizopus rhizopodiformis* III-59 (CBS 221.80)
*Rhizopus rhizopodiformis* III-65 (CBS 222.80)

The preparation and isolation of the mutants is effected in the following manner, and this process for producing the above mutants is another feature of the invention:

Slant cultures of the wild strain Rhizopus CBS 227.75 that had formed spores on brewers wort broth agar were eluted with sterile 0.005% sodium laurylsulfate solution, the spore suspension was filtered through a sterile glass sieve (D-3) to separate the mycelium fragments, followed by 15 minutes centrifuging at 6000 rpm. The sedimented spores were taken up in sterile 0.1M acetate buffer (pH 4.5) and the concentration of the spores under the microscope was adjusted to approximately $10^8$ spores/ml. The adjusted spore solution was then irradiated under an ultraviolet lamp (wave length 254 nm, 13 Watt) until a kill factor of 99.9% was reached. The irradiated spores were spread on plates of casein agar of the following composition:

0.10% Soybean flour
0.10% Corn steepwater
0.50% Glucose
0.50% Gelatin
0.50% Malt extract
0.10% Sodium desoxycholate
0.24% $KH_2PO_4$
0.10% $MgCL_2.6H_2O$
0.05% $MnSO_4.4H_2O$
0.02% $CaCl_2.2H_2O$
0.04% Casein
1.60% Agar
pH 5.5

The plates were incubated for two to three days at 30° C. Only colonies with an intense caseolytic aura were then isolated as strain cultures and tested further.

The new strains were cultivated in agitated cultures at 30° C. to screen their proteolytic synthesis capacity (500 ml Erlenmeyer flask with baffles, agitation frequency 150 rpm). The composition of the culture medium was as follows:

0.25% $KH_2PO_4$
0.06% $NaNO_3$
2.00% Casein
0.80% Gelatin
0.50% Soybean flour
0.50% Malt extract
2.00% Corn starch(amylolysis)
10.00% Vol. of wheat bran extract (20%)
10.00% Vol. of oat meal extract (10%)
pH 5.5

In this manner, a series of mutant strains with distinctly higher protease activity were isolated from the wild strain. With the most active of these strains, further mutation experiments were undertaken, which lead to strains with still higher activity. These experiments were repeated for a total of three times and all of the following strains were isolated and the protease yield determined.

TABLE 1

| STRAINS | GENERATION | PROTEASE ACTIVITY (mTU/ml) |
|---|---|---|
| Wildstrain CBS 227.75 | | 8 |
| Strain I-261 | 1 | 15 |
| Strain I-266 | 1 | 18 |
| Strain II-47 | 2 | 20 |
| Strain III-34 | 3 | 37 |
| Strain III-44 | 3 | 37 |
| Strain III-46 | 3 | 32 |
| Strain III-59 | 3 | 28 |
| Strain III-65 | 3 | 21 |

Of these strains, the following were deposited in the Centraal Bureau voor Schimmel-Cultures in Baarn (the Netherlands):

TABLE 2

| STRAIN | DEPOSITORY # | DAY OF DEPOSIT |
|---|---|---|
| III-34 | CBS 219.80 | 3 APR 80 |
| III-46 | CBS 220.80 | 3 APR 80 |
| III-59 | CBS 221.80 | 3 APR 80 |
| III-65 | CBS 222.80 | 3 APR 80 |

Proteases produced by the strains of Table 1 have the same properties as the protease produced by wild strain CBS 227.75. The proteases of the invention are characterized by a particularly broad activity spectrum in the weakly acid region between a pH of 2.5 and a pH of 6.5. The optimum activity is at a pH of 4.5; the range of 80% maximum activity is from a pH of 3.3 to a pH of 5.9; the range of 60% maximum activity is from a pH of 3.0 to a pH of 6.5. The proteases prepared by the mutants of the invention are particularly suitable for use as additives in animal feeds, especially to improve the results of raising and fattening poultry, pigs, calves, and commercially raised fish. Moreover, they can also be employed for other purposes where acid stable proteases are used, for example, in the food processing industry, in acid detergents for washing and cleaning, especially in cleaners for tiles, floors and tables, in hospitals and in households, as an aid in tanning leather, and also in highly purified form as digestives in medical applications.

The process for the production of protease can be carried out by culturing the selected mutants in a liquid or solid nutrient medium, but a liquid nutrient medium is generally preferred. Culturing in a nutrient solution is carried out according to usual procedures for aerobic agitation.

The nutrient medium to be used in accordance with the invention is prepared by conventional means and should contain a carbon source, a nitrogen source and other nutrients and growth substances needed by the microorganism. Suitable carbon sources include starch, dextrin, sucrose, glucose, fructose, maltose and sugar-containing waste materials. Suitable nitrogen sources include ammonium salts, urea, casein, gelatin, corn steepwater and soybean flour or soybean cakes. Furthermore, inorganic salts such as sodium hydrogen phosphate, potassium hydrogen phosphate, ammonium hydrogen phosphate, and calcium and magnesium salts may be added to the nutrient medium. Furthermore, it may be advantageous to add growth-promoting substances such as yeast extract and vitamins to the nutrient medium.

The fermentation temperature may fluctuate between about 25° C. and about 50° C., but should preferably be between about 27° C. and about 32° C. The pH of the nutrient medium may be between about 3.0 and about 7.0, preferably between about 4.0 and about 6.0. Generally, culturing is carried out over a period of 20 to 96 hours.

The proteases produced in accordance with the process of the invention can be precipitated and concentrated from the filtered or centrifuged nutrient solution by conventional methods through the addition of organic solvents or through salting out with, e.g., sodium sulfate or ammonium sulfate. The proteases can be purified by dialysis or by treatment with ion exchange resins.

The proteolytic activity of the above proteases was determined according to the known principle of determination according to Anson: a suitably diluted amount of enzyme solution was incubated at 40° C. for 20 minutes with an equal volume of a 1.2% casein solution, which contained 0.6% lactic acid, 6 moles of urea and 0.1 mole of citric or acetic acid. The pH of the casein solution was adjusted to 4.5 by adding 2N caustic soda solution. After the incubation, 0.4N trichloroacetic acid was added in a 1:1 volume ratio. The precipitate formed was filtered off from the undigested casein, and the protein fragments in the filtrate formed during the decomposition were determined according to any known protein determination method. Suitable, e.g., is the procedure described by Layne in Methods of Enzymology 3 (1957), pages 448 et seq.

For each determination, a blank must be determined by first adding trichloroacetic acid and then the casein solution. This blank value indicates that portion of low molecular weight peptides which was already present in the enzyme solution before digestion. When compared to the reagent standard, the difference between principal and blank values is compared in the indicated method with the extinction which a known amount of tyrosine supplies in this determination.

This amount of tyrosine is then a measure of the proteolytic activity of the foregoing enzyme. An enzyme unit (TU) is that amount of enzyme which causes the same extinction difference between the principal and blank values per minute as 1M tyrosine solution which is used instead of the enzyme solution.

The measurement of the proteolytic activity at pH values higher and lower than 4.5 can be carried out without difficulty by suitable standardization of the casein solution, but in this case the acetic acid is preferably replaced by citric acid.

EXAMPLE 1

In preparing the nutrient medium, 3 g of soybean flour, 3 g of corn steepwater, 15 g of casein, 7 g of gelatin, 2.4 g of $KH_2PO_4$, 0.5 g of $MgSO_4.7H_2O$, 0.1 g of $MnCl_2.4H_2O$, 0.1 g of $CaCl_2.2H_2O$ and 20 g of cornstarch were dissolved or dispersed in 1 liter of water. The pH of the nutrient solution was 5.3. The cornstarch was largely broken down by amylase. The sterilized nutrient solution was inoculated with spores of the mutant III-34 and the culture was grown in an agitation incubator under optimal aeration at 30° C. for about 50 hours. After this time, the fungus mycelium was filtered off and the mycelium-free culture broth was used for the determination of protease activity in accordance with the above described method. It was found that the culture solution attained an enzymatic activity of 37 mTU/ml.

EXAMPLE 2

In preparing the nutrient medium, 10 g of soybean flour (oil-free), 5 g of corn steepwater, 12 g of casein, 5 g of gelatin, 5 g of dry grain slop, 2.4 g of $KH_2PO_4$, 1 g of $NaNO_3$, 1 g of $NH_4Cl$, 0.01 g of $FeSO_4$ and 30 g of native cornstarch were dissolved or dispersed in one liter of tap water. The pH of the nutrient solution was adjusted to 5.3 after autoclaving. 10 ml of a Czapek-Dox preliminary culture (with 5% starch and 0.5% yeast extract) was added to a 1 liter Erlenmeyer flask charged with the above nutrient solution. This nutrient solution was inoculated with spores of the mutant III-59 and agitated for 24 hours at 30° C., and aerated at 30° C. for about 72–96 hours until the pH had risen to 6.8–7.0. The mycelium was then filtered off and the clear culture broth used for the determination of protease activity according to the above described method. It was found that the culture solution attained an enzymatic activity of 28 mTU/ml.

The protease was isolated by clarification/filtration of the broth contained in 10 1 liter agitation flasks after adding 5 g of Filter Cel and 5 g of standard Super Cel from Mansville Corp., concentrated at 50 Torr to one-third of the initial volume, and precipitated by adding 39% of anhydrous sodium sulfate with agitation, whereby the temperature increased to 39°–40° C. Alternatively, the protease may also be precipitated by dropwise addition of 2 volumes of ethanol, methanol, acetone or other water-miscible solvent at a temperature of −3° C. to 5° C. The precipitate was removed and dried under vacuum.

EXAMPLE 3

Using the above described determination process, the activity of the protease isolated according to Examples 1 and 2 was determined in relation to the pH. Table 3 below contains the pH range for optimum activity and for 50% of the optimum activity measured at the optimum pH range. The values indicate that the proteases of the mutants used in Examples 1 and 2 have the same favorable broad pH activity spectrum for the above-mentioned applications as the protease isolated from the wild form CBS 227.75.

TABLE 3

| Enzyme | pH for optimum activity | pH for 50% of optimum activity |
|---|---|---|
| Protease from Mutant III-34 | 4.0-4.5 | 2.5-6.5 |
| Protease from Mutant III-59 | 4.0-4.5 | 2.5-6.5 |
| Protease from CBS 227.75 | 4.0-4.5 | 2.5-6.5 |

EXAMPLE 4

The proteases obtained from the mutants *Rhizopus rhizopodiformis* III-34, III-46, III-59 and III-65 were compared by the method of isoelectrofocussing or cross-reaction of Ouchterlony with the protease obtained from the wild strain CBS 227.75. In this manner, the complete identity of all proteases was established.

the current intensity increased to 15 mA. The separation was completed after 2 to 2.5 hours.

Determination of the pH gradients

The pH gradient was determined with a calibrated surface pH electrode so as to provide readings of pH fluctuations between the anode and the cathode at several lines; a pH/cm diagram was constructed therefrom.

Fixing and Staining

Fixing solution: Distilled water was added to 57.5 g of trichloroacetic acid and 17.25 g of sulfosalicylic acid until the solution reached 500 ml.

Destaining: A mixture of 500 ml ethanol and 160 ml acetic acid was diluted with distilled water to 2000 ml.

Staining solution: 0.46 g Coomassie Blue G-250 in 400 ml destaining solution.

After construction of the pH profile, the gel was left for one hour in an agitated fixing solution to achieve protein precipitation and Ampholine removal, then washed for 5 minutes with destaining solution, followed by 10 minutes in staining solution at 60° C. The gel was destained by changing the destaining solution several times until the blue colored protein strips were clearly brought out from the background.

The isoelectric points of proteins were determined by means of the pH profile.

Description of the method of cross reaction according to Ouchterlony

Material:

Immunodiffusion plates (Code No. 64-276-1) made by Miles, Frankfurt, were used for the cross reaction. The pre-prepared plates contain 0.9% agarose in a borate/sodium chloride buffer, pH 7.5, ionic strength 0.175%.

TABLE 4

| | Results of Isoelectrofocussing Protein zone with pI | | | | | | | | | | Immunological Test Cross reaction of Ouchterlony with CBS 227.75 |
|---|---|---|---|---|---|---|---|---|---|---|---|
| | 4.7 | | 4.9 | | 5.1 | | 5.4 | | 6.1 | | |
| | a | b | a | b | a | b | a | b | a | b | |
| Wild strain CBS 227.75 | X | X | XX | XX | XXX | XXX | XX | XX | XX | XX | + |
| Mutants III-34 | X | X | XX | XX | XXX | XXX | XX | XX | XX | XX | + |
| III-46 | X | X | XX | XX | XXX | XXX | XX | XX | XX | XX | + |
| III-59 | X | X | XX | XX | XXX | XXX | XX | XX | XX | XX | + |
| III-65 | X | X | XX | XX | XXX | XXX | XX | XX | XX | XX | + | a Coomassie-blue Reaction (Protein)
b Zymogramm - Reaction (Protease)

Description of the method of isoelectrofocussing

Equipment: Multiphor 2117, LKB Instruments LKB 2103 Power Supply

Material: LKB Ampholine PAG plates, LKB Instruments, pH 3.5-9.5

Anode solution: 1M H3PO4
Cathode solution: 1M NaOH

Isoelectrofocussing

After application of the polyacrylamide gel to the water-cooled apparatus, the electrode solution soaked paper electrode strips were placed on the border of the gel. 5 mm wide filter strips were placed on the center line of the gel between the anode and the cathode and 10 μl of a salt-free test solution (5 mg/ml protein) was added dropwise. After the apparatus was closed, the pH gradient was built up to a current intensity of 10 mA, the test filter strips were removed after 30 minutes and In addition, the plates contain 0.01% thiomersal as a bacteriostatic agent and trypan blue as an indicator for the protein precipitation lines.

Protease CBS 227.75 antibodies were obtained from rabbits.

Protease CBS 227.75 serves as positive control for immunization.

Procedure:

25 μl of antiserum was pipetted into the middle of the diffusion plates and 25 μl of protease solution in a concentration of 5 mg/ml or 10 mg/ml was pipetted into each of the external holes.

Diffusion time: 72 hours at 4° C.

The precipitation lines may be detected by means of the trypan blue indicator in the agarose. The immunological cross reaction is then only positive if the antibody producing protease is identical to the tested protease. This is ascertained by blending the precipitation lines.

What is claimed is:

1. A process for the preparation of an acid stable protease having a broad pH-activity spectrum comprising the steps of
   (a) culturing a mutant form of a fungus strain of the genus Rhizopus, wherein said mutant has enhanced protease forming ability compared to its parent strain, in a nutrient medium containing assimilable carbon and nitrogen sources at a pH between about 3 and about 7 and at a temperature between about 25° C. and about 50° C. to form an acid stable protease; and
   (b) separating said protease from the nutrient medium; wherein said mutant in step (a) is selected from the group consisting of mutants having the following depository designations:
   (a) *Rhizopus rhizopodiformis* III-34 (CBS 219.80);
   (b) *Rhizopus rhizopodiformis* III-46 (CBS 220.80);
   (c) *Rhizopus rhizopodiformis* III-59 (CBS 221.80); and
   (d) *Rhizopus rhizopodiformis* III-65 (CBS 222.80).

2. A process in accordance with claim 1 wherein said mutant is obtained by UV irradiation.

3. A process in accordance with claim 1 wherein said mutant has a proteolytic activity of >10 mTU/ml in agitated cultures.

4. A process in accordance with claim 1 wherein said mutant has a proteolytic activity of at least 21 mTU/ml in agitated culture.

5. A culture consisting essentially of a mutant form of the fungus strain *Rhizopus rhizopodiformis* CBS 227.75 selected from the group consisting of mutants having the following depository designations:
   (a) *Rhizopus rhizopodiformis* III-34 (CBS 219.80);
   (b) *Rhizopus rhizopodiformis* III-46 (CBS 220.80);
   (c) *Rhizopus rhizopodiformis* III-59 (CBS 221.80); and
   (d) *Rhizopus rhizopodiformis* III-65 (CBS 222.80).

6. A method of producing a mutant form of the fungus strain *Rhizopus rhizopodiformis* CBS 227.75 comprising exposing spores of the fungus strain to UV irradiation until a high kill rate of the spores is obtained, culturing the irradiated fungus spores in or on a nutrient medium which contains casein, isolating therefrom colonies having a strong caseolytic aura, separately cultivating the isolated colonies in agitated nutrient media, and isolating therefrom the following mutant strains having protease activity higher than that of the parent strain:
   (a) *Rhizopus rhizopodiformis* III-34 (CBS 219.80);
   (b) *Rhizopus rhizopodiformis* III-46 (CBS 220.80);
   (c) *Rhizopus rhizopodiformis* III-59 (CBS 221.80); and
   (d) *Rhizopus rhizopodiformis* III-65 (CBS 222.80).

7. A method in accordance with claim 6 wherein the most proteolytically active strains obtained by said method are then used as the strains for at least one additional treatment in accordance with said method.

* * * * *